United States Patent [19]

Nakagawa et al.

[11] Patent Number: 5,491,151
[45] Date of Patent: Feb. 13, 1996

[54] ANTITUMOR TREATMENT METHOD

[75] Inventors: Yoshinori Nakagawa; Tetsuo Kimoto; Makoto Takeuchi, all of Okayama, Japan

[73] Assignee: Kabushiki Kaisha Hayashibara Seibutsu Kagaku Kenkyujo, Okayama, Japan

[21] Appl. No.: 486,615

[22] Filed: Jun. 7, 1995

Related U.S. Application Data

[63] Continuation of Ser. No. 203,747, Mar. 1, 1994, abandoned, which is a continuation of Ser. No. 894,686, Jun. 5, 1992, abandoned, which is a division of Ser. No. 570,455, Aug. 21, 1990, abandoned.

[30] Foreign Application Priority Data

Aug. 30, 1989 [JP] Japan ................................. 1-224165

[51] Int. Cl.$^6$ ................................................. A61K 31/47
[52] U.S. Cl. ......................... 514/311; 514/301; 514/367; 424/422
[58] Field of Search .................... 424/422, 301; 514/311, 367; 8/569; 436/800

[56] References Cited

U.S. PATENT DOCUMENTS

| | | | |
|---|---|---|---|
| 4,959,301 | 9/1990 | Weaver | 435/177 |
| 5,091,385 | 2/1992 | Gulliya | 514/410 |

FOREIGN PATENT DOCUMENTS

| | | |
|---|---|---|
| 0286252 | 10/1988 | European Pat. Off. . |
| 209019 | 9/1987 | Japan . |

OTHER PUBLICATIONS

Minani Chem Pharm Bull 30, p. 3106 (1982).

*Primary Examiner*—Gollamudi S. Kishore
*Attorney, Agent, or Firm*—Browdy and Neimark

[57] ABSTRACT

This invention relates to an antitumor agent containing as the effective ingredient a cyanine dye, shown by the general formula:

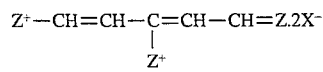

where $X^-$ is a physiologically-acceptable anion; $Z^+$, a group of the formula

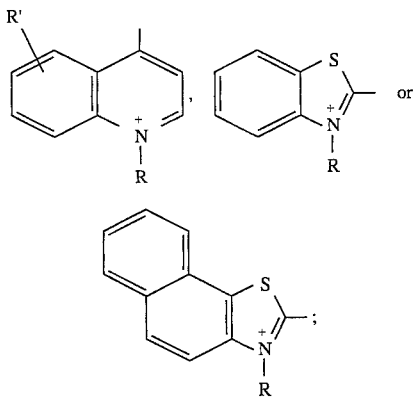

R, an alkyl group having a carbon chain length of 1–5; and R', either hydrogen atom or an alkoxy group. Oral and parenteral administration of the antitumor agent remarkably activates macrophages in vivo and enhances their functions to allow them to inhibit the growth and metastasis of tumors, as well as to accelerate their natural death through cicatrization.

6 Claims, No Drawings

ANTITUMOR TREATMENT METHOD

This application is a continuation of application Ser. No. 08/203,747, filed Mar. 1, 1994 now abandoned; itself a continuation of parent application Ser. No. 07/894,686 filed Jun. 5, 1992, now abandoned; which itself is a division of grandparent application Ser. No. 07/570,455 filed Aug. 21, 1990, now abandoned.

BACKGROUND OF THE INVENTION

1. Field of the Invention

The present invention relates to an antitumor agent, in particular, a novel antitumor agent containing as the effective ingredient a cyanine dye.

2. Description of the Prior Art

Generally, antitumor agents can be briefly grouped into antibiotic and immunological types. Since both types of antitumor agents do not distinguish between tumor and normal cells, they are strongly toxic to normal cells and unpromising in the conquest of malignant tumors.

Recently highlighted is "Biological Response Modifier (abbreviated as "BRM" hereinafter)", a substance regulating the response in living body and useful in the treatment of malignant tumors in vivo. Most of the BRMs which are in earnest investigation are proteinaceous substances from animal as is the case, for example, of interferon, tumor necrosis factor, lymphotoxin and interleukin. Such proteinaceous BRMs have the disadvantage that their large-scale preparation in high-purity and pyrogen-free form is very difficult because they are usually produced in a culture of hemopoietic cells or micro-organisms wherein the BRM production gene has been introduced by the gene recombinant technique, as well as the advantage that they cause less toxicity and side effect because they are inherently produced in vivo.

Furthermore, most of the proteinaceous BRMs exhibit no antitumor activity when orally administered. Thus, any BRM antitumor agent which is efficacious through oral administration has been highly sought after.

Summary of the Invention

In view of the foregoing, we investigated various BRM substances, in particular, cyanine dyes which are produceable in high-purity and large-scale by chemical synthesis, as well as exhibiting a strong antitumor activity with less toxicity and side effect when administered in living body.

As the result, we found that when injected in the interstitial tissue in tumors, the cyanine dye shown by the general formula:

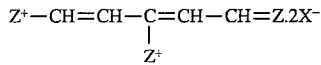

wherein $X^-$ is a physiologically-acceptable anion; $Z^+$,

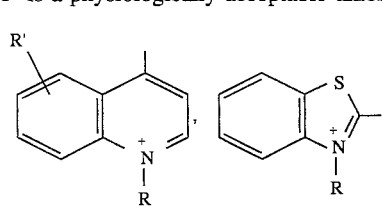

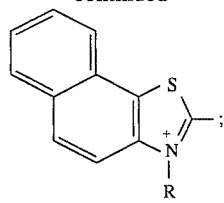

Z, the same as $Z^+$ but without the positive charge; R, an alkyl group having a carbon chain length of 1–5; and R', either hydrogen atom or an alkoxy group does activate macrophages and improve their functions to enhance the stromal reactions in a living body specific and nonspecific to the tumors. Such an enhancement leads to a remarkable antitumor effect which inhibits the growth and metastasis of the tumors, as well as accelerating their natural death and cicatrization. Also was found that the cyanine dye is safely and conveniently usable over a long period of time because the objective is attainable with a relatively small dose of the cyanine dye.

Detailed Description of the Invention

The cyanine dye used in the invention shown by the general formula:

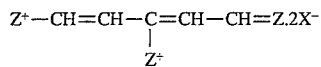

is a pentamethine cyanine dye which inhibits the growth and metastasis of tumors when administered in animals, as well as accelerating the regression and natural death of the tumors.

In the formula, $X^-$ represents a physiologically-acceptable anion, for example, halides such as chloride, bromide and iodide; inorganic anions such as sulfuric ion, nitric ion and perchloric ion; organic sulfonic ions such as p-toluenesulfonic ion; organic carboxylic ion such as acetic ion; and other organic anions such as nicotinic ion and orotic ion.

$Z^+$ represents a heterocyclic group of the formula

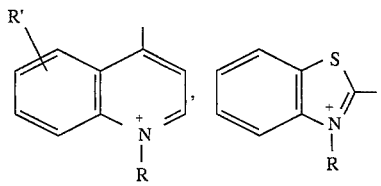

or

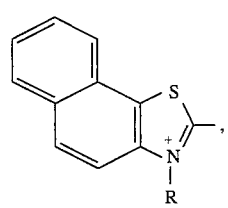

provided that when $Z^+$ is a group of the formula

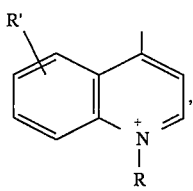

R' is either hydrogen atom or an alkoxy group having a carbon chain length of 1–3, preferably, ethyxoy group.

R represents a normal or branched alkyl group having a carbon chain length of 1–5, for example, methyl group, ethyl group, n-propyl group, isopropyl group, n-butyl group and isopentyl group, preferably, ethyl group.

Particularly, the cyanine dye designated as "LUMIN" where $Z^+$, R and $X^-$ in the general formula are a group of the formula

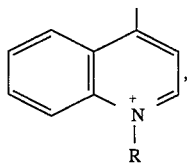

ethyl group and iodide respectively, a chemical formula of [bis-4-(ethylquinoline)][γ-4'-(1-ethylquinoline)] pentamethine cyanine diiodide, is favorably usable in this invention.

These cyanine dyes are preparable by conventional method as described, for example, in K. Ven Kataraman, *The Chemistry of Synthetic Dyes*, Vol.2, pp.1143–1186, published by Academic Press Inc., London (1952), T. Ogata, *Kankho-shikiso* (*Photosensitizing Dyes*), published by Sankaido Publishing Co., Tokyo, Japan (1933), and T. Ogata, *Kankho-sei Shikiso* (*Photosensitive Dyes*), published by Iwanami Shoten Publishers, Tokyo, Japan (1933), if necessary, with a slight modification.

The antitumor agent of this invention exhibits a superior antitumor activity on various tumors in warm-blooded animals, in particular, mammals, for example, human, monkey, dog, mouse and rat. The antitumor agent exhibits an extremely high inhibitory activity on malignant tumors wherein a collagenic increment is observed; for example, stomach cancer, lung cancer, liver cancer, uterine cancer, breast cancer, malignant melanoma and skin cancer.

The antitumor agent of this invention can be prepared, for example, into injections, powders, granules, tablets, capsules and suppositories for oral and parenteral administration alone or in combination with a physiologically-acceptable carrier, excipient, diluent and, if necessary, other BRM antitumor agent, for example, interferon, tumor necrosis factor, lymphotoxin and interleukin.

The antitumor agent of this invention includes a medicine in unit dose form. By the wording "medicine in unit dose form" is meant a medicine containing a daily dose of the above described cyanine dye, as well as its multiples (up to 4 times) and measures (down to 1/40), which are in a physically separated unit form suitable for administration. As a medicine in such a unit dose form, there may be mentioned, for example, injections, powders, tablets, capsules and suppositories. When the cyanine dye to be used is sensitive to electromagnetic waves such as infrared rays, it is desirable to employ a ready-mix-type dose form.

The dose of the antitumor agent of this invention is generally very low dependently on the type of tumor, symptom, administration route and dose form; desirably, as the cyanine dye, about 0.1–50 μg/kg(body weight)/day for adult, preferably, about 0.5–10 μg/kg(body weight)/day for adult.

The cyanine dye used in this invention attains a remarkable antitumor effect when administered even in such a small dose. This is because the administration of the cyanine dye extremely activates macrophages which specifically attack tumoral tissues.

More particularly, we found that the presence of an appropriate concentration of the cyanine dye activates macrophages generally by about 1.5-fold higher or more, desirably, about 2-fold higher or more. The activated macrophages specifically attack tumoral tissues to inhibit their growth and metastasis, as well as to accelerate their natural death through cicatrization when collected in and around the tumoral tissues.

Antitumor agents utilizing any cytotoxicity of compounds have the disadvantage that they nonspecifically attacks normal cells in addition to tumor cells. This may seriously damage normal cells. While the antitumor agent of this invention is characterized in that it substantially does not affect normal cells even when administered over a long period of time.

The cyanine dye used in this invention is characterized in that, unlike proteinaceous BRMs from animals, it is more easily preparable in a large-scale, as well as that a pyrogen-free, high-purity preparation is obtainable at a low cost unlike the case of proteinaceous BRMs from animals where a trace of BRM in a culture of animal cell or microorganism is recovered through a number of complicated purification steps.

In use, when the cyanine dye in the antitumor agent is low in the ability of collecting macrophage, the objective is attainable by increasing the difference between normal and tumor cells in quality by:

(i) a method wherein a tumoral tissue is slightly damaged by heating the tumoral site before, during or immediately after the administration of the antitumor agent;

(ii) a method wherein after an occasional administration of porphyrin pigment to tumoral tissue, either an electromagnetic wave such as infrared ray or a radiation such as that from $^\alpha$Co is irradiated to the tumoral tissue; or (iii) a method wherein another antitumor agent such as bleomycin or BCG vaccine with a reduced concentration, generally, about 1/20 or lower of their usual dose, is used in combination.

In case of irradiating with an electromagnetic wave, a light having a wavelength within the absorption band of the cyanine dye to be used, generally, a near infrared ray is irradiated for about one minute or longer, preferably, about 5 minutes or longer during or immediately, particularly, within 5 minutes after the administration of the antitumor agent using, desirably, an infrared lamp or a laser emitter.

Combination of the antitumor agent of this invention with hyperthermia may attain a remarkable antitumor effect. More particularly, a synergistic effect which is greater than the sum of their individual effects may be attained by soaking a tumoral site in a water bath at a temperature of about 38°–47° C., preferably, about 40°–44° C. for about 15 minutes or longer, preferably, about 30 minutes or longer during or immediately before or after the administration of the antitumor agent. Since, unlike administration of any radiation or other antitumor agent, hyperthermia can be readily carried out at home, such a combination is very convenient in home treatment.

The macrophages which have been activated with the cyanine dye are collected in and around a tumoral tissue, and then allowed to increase the specific and nonspecific stromal reactions in living body to enhance its protective reaction to the tumor. The macrophages simultaneously enhance the production of collagenic fiber in and around the tumoral tissue while inhibiting its growth, thus enclosing the tumoral tissue and accelerating its natural death through cicatrization.

In a home treatment using conventional antitumor agent which is efficacious only through injection, patients have to apply an injection by themselves. In case of intravenous injection, no patient can easily do it because of fear. While the antitumor agent of this invention is favorably usable in the prevention of tumoral recurrence in home treatment because it attains an extremely high antitumor effect even through oral administration.

The following in vitro and in vivo experiments will explain the macrophage-activating activity, antitumor activity and toxicity of the cyanine dye used in this invention.

EXPERIMENT 1

Activation of Macrophage by Cyanine Dye

Compound No.1–7, which bears $Z^+$ as in the general formula a group of the formula

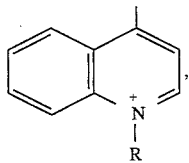

as well as bearing R and $X^-$ as shown in Table I, and Compound No.8, which bears as $Z^+$ in the general formula a group of the formula

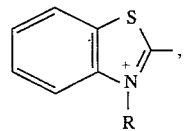

as well as bearing R and $X^-$ as shown in Table I, were tested for their macrophage-activating activity using groups of seven BALB/c mice, 8 week old each.

More particularly, either of Compounds No.1–8 in Table 1 was first dissolved or suspended in saline, then intraperitoneally administered in the mice in a dose of 50 ng/0.2 ml/animal. Two days after the administration, the ascites of the mice were extracted, and the cells which adhered onto plastic Petri dish were collected. To $2 \times 10^4$ of the adhering cell was added $1 \times 10^3$ Meth A ascitic tumor cells, and the mixture was cultured for 24 hours in RPMI 1640 medium supplemented with fetal calf serum, added with $^3$H-thymidine, and incubated for an additional 16 hours.

Control group was intraperitoneally administered with 0.2 ml saline.

TABLE I

| Compound No. | R | $X^-$ | Melting point (°C.) |
|---|---|---|---|
| 1 | $C_2H_5$ | I | 281–283 |
| 2 | $C_2H_5$ | Cl | 245–248 |
| 3 | $C_2H_5$ | Br | 266–269 |
| 4 | $C_2H_5$ | ClO4 | 268–272 |

TABLE I-continued

| Compound No. | R | $X^-$ | Melting point (°C.) |
|---|---|---|---|
| 5 | $C_2H_5$ | ![structure] | 240–243 |
| 6 | $CH_3$ | I | 278–282 |
| 7 | $n-C_4H_9$ | I | 236–239 |
| 8 | $CH_3$ | I | 238–242 |

Thereafter, the incorporation of $^3$H-thymidine in the tumor cell was determined by conventional method, and the growth inhibitory rate for tumor (%) was calculated with the following equation. The macrophage activation by Compounds No.1–8 was evaluated using their growth inhibitory rate as the criterion.

$$\text{Growth inhibitory rate for tumor (\%)} = \frac{A - B}{A} \times 100$$

where A is the mean incorporation found in the control group, and B is that found in the test group.

The results were as shown in Table II.

The results in Table II evidently confirm that a relatively small dose of the cyanine dye used in this invention remarkably activates macrophages.

The following animal experiments will explain the efficacy of the antitumor agent of this invention. These experiments proved the efficacy using mice as the model. It has been established that the below described tumors in rodents are reliable models for tumors in other warm-blooded animals.

TABLE II

| Compound No. | Growth inhibitory rate (%) |
|---|---|
| 1 | 25.1 |
| 2 | 44.5 |
| 3 | 32.3 |
| 4 | 36.2 |
| 5 | 27.5 |
| 6 | 41.8 |
| 7 | 37.6 |
| 8 | 27.3 |

EXPERIMENT 2

Antitumor Activity of Cyanine Dye

Experiment 2-1
Antitumor effect on tumor-bearing mouse

Compounds No.1, 7 and 8 in Table I were evaluated for their antitumor activity using as the criterion the life-span increasing effect on tumor-bearing mice which had received the transplantation of Meth A ascitic tumor cell.

More particularly, 8 week-old male BALB/c mice were intraperitoneally transplanted with $1 \times 10^5$ cells/mouse of Meth A cell. Ten days after the transplantation, a group of seven mice with a successful transplantation were intraperitoneally administered with either Compound No.1, 7 or 8 in Table I twice a week over a period of 40 days while monitoring the mice.

Control group was intraperitoneally administered with 0.2 ml saline in accordance with the same administration schedule.

The rate of increase in life-span (T/C %) under the above conditions was calculated from the mean survival days found for the test group (T) and control group (C).

Rate of increase in life-span (T/C %) =

$$\frac{\text{Mean survival days of the test group}}{\text{Mean survival days of the control group}} \times 100$$

The results were as shown in Table III.

TABLE III

| Compound No. | Dose (ng/0.2 ml/animal) | Mean survival days* | Survivals after 40 days | Increase in life-span (T/C %) |
|---|---|---|---|---|
| Control | — | 29.6 ± 1.6 | 0 | 100 |
| 1 | 50 | 45.6 ± 4.2 | 6 | 154 |
|  | 5 | 48.9 ± 4.2 | 7 | 165 |
|  | 0.5 | 36.1 ± 4.3 | 2 | 122 |
| 7 | 50 | 39.9 ± 5.4 | 4 | 135 |
|  | 5 | 42.9 ± 6.0 | 5 | 145 |
|  | 0.5 | 31.1 ± 4.2 | 0 | 105 |
| 8 | 50 | 43.7 ± 4.0 | 6 | 148 |
|  | 5 | 49.3 ± 5.6 | 7 | 167 |
|  | 0.5 | 34.4 ± 5.7 | 1 | 116 |

Note: (*) means that the values are statistically significant to the control at a significant level of 5% or lower.

The results in Table III evidently confirm that a relatively small dose of the cyanine dye used in this invention attains a remarkable life-span increasing effect on syngenic tumor-bearing mice.

Experiment 2-2
Antitumor effect by growth inhibition of tumor

Compounds No.1, 7 and 8 in Table I were evaluated for their antitumor activity using as the criterion the growth inhibitory effect on MC-1 cell, a methylcholanthrene-induced syngenic tumor.

Eight week-old female C57BL/6 mice were subcutaneously transplanted in their dorsum area with $1 \times 10^5$ cells/animal of MC-1 cell. Five days after the transplantation, a group of seven mice with a successful transplantation were subcutaneously administered with either Compound No.1, 7 or 8 in Table I twice a week over a period of 25 days while monitoring the mice.

One another group of mice were light-irradiated with 100 W medical infrared lamp (100 V) placed about one meter in apart immediately after every administration of either Compound No.1, 7 or 8.

Control group was subcutaneously administered with 0.2 ml saline in accordance with the same administration schedule.

TABLE IV

| Compound No. | Dose (ng/0.2 ml/animal) | Mean wet weight of tumor* (g) | Rate of survival (%) |
|---|---|---|---|
| Control | — | 4.5 ± 0.6 (4.5 ± 0.7) | 85.7 |
| 1 | 50 | 3.7 ± 0.2 (1.5 ± 0.3) | 100 (100) |
|  | 5 | 3.1 ± 0.4 (0.8 ± 0.1) | 100 (100) |
|  | 0.5 | 4.1 ± 0.5 (2.8 ± 0.3) | 85.7 (100) |
| 7 | 50 | 4.0 ± 0.4 (2.6 ± 0.5) | 85.7 (100) |
|  | 5 | 3.5 ± 0.8 (1.9 ± 0.8) | 100 (100) |
|  | 0.5 | 4.7 ± 1.0 (3.3 ± 0.6) | 71.4 (85.7) |
| 8 | 50 | 3.5 ± 0.5 (1.2 ± 0.2) | 85.7 (100) |
|  | 5 | 2.9 ± 0.9 (0.5 ± 0.5) | 100 (100) |
|  | 0.5 | 3.6 ± 0.4 (2.9 ± 0.7) | 71.4 (100) |

Note: (*) means that the values are significant to the control at a significant level of 5% or lower. The values in the parenthesis represent mean wets weight of tumor and rates of survival (%) when combined with light-irradiation.

On the 27th day after the transplantation, the wet weight of tumor was determined by the method in Y. Shimosato and N. Tamaoki, *Human Cancer and Nude mice*, pp. 321–323, published by Ishiyaku Publishers Inc., Tokyo, Japan (1982), as well as monitoring the rate (%) of survivals on the 35th day.

The results were as shown in Table IV.

The results in Table IV evidently confirm that a small dose of the cyanine dye used in this invention remarkably inhibits the growth of a syngenic tumor.

Also is confirmed that the light-irradiation remarkably enhances the growth inhibition.

Experiment 2-3
Synergistic effect by the combination with hyperthermia

Compounds No. 1, 7 and 8 were evaluated for their synergistic effect when combined with hyperthermia using as the criterion the growth inhibitory effect on Meth A ascitic tumor.

More particularly, 6 week-old BALB/c mice were subcutaneously transplanted in their femoral area with $2 \times 10^5$ cells/animal of Meth A cell. A group of five mice with a successful transplantation were subcutaneously administered in their femoral area with either Compound No.1, 7 or 8 in Table I in a dose of 20 ng/0.1 ml/animal twice a week. Immediately after every administration, the tumoral sites of the mice were soaked in about 42° C. water bath for about 60 minutes. On the 40th day after the transplantation, the mean wet weight of tumor was determined by the method in Experiment 2-2.

Separately, one of other groups was administered with either cyanine dye, and determined for its mean wet weight of tumor, while one another group was first administered with saline, then subjected to hyperthermia, followed by determining the mean wet weight of tumor.

Control group was subcutaneously injected with 0.1 ml saline in the femoral area.

The mean wet weights of tumor were put into the following equation to calculate the growth inhibitory rate for tumor (%) which was then used to evaluate any synergistic effect by the combination of cyanine dye and hyperthermia.

Growth inhibitory rate for tumor (%) =

$$\frac{\text{Mean wet weight of tumor in the test group}}{\text{Mean wet weight of tumor in the control group}} \times 100$$

The results were as shown in Table VI.

The results in Table VI evidently confirm that the combination of the antitumor agent of this invention with hyperthermia attains a remarkable synergism which leads to an antitumor effect about 3-fold higher than that attained by the sole use of the cyanine dye.

TABLE VI

| Treatment | Mean wet weight of tumor (g) | Growth inhibitory rate for tumor (%) |
|---|---|---|
| Control | 4.91 ± 0.94 | 100 |
| Hyperthemia | 3.76 ± 0.98 | 76.3 |
| Compound No.1 | 3.24 ± 1.45 (0.12 ± 0.15) | 65.9 (2.4) |
| Compound No.7 | 3.35 ± 1.75 (0.62 ± 0.45) | 68.2 (12.6) |
| Compound No.8 | 3.40 ± 1.38 (0.90 ± 0.66) | 69.2 (18.3) |

Note: (*) means that the values are statistically significant to the control at a significant level of 5% or lower. The values in parenthesis represent mean wet weights of tumor and growth inhibitory rates for tumor when combined with hyperthemia.

EXPERIMENT 3

Acute Toxicity

Either of Compounds No.1–8 in Table I was dissolved or suspended in saline containing 5% gum arabic, and a group of ddy mice, about 10–20 g each, received an intraperitoneal or oral administration of the resultant mixture occasionally through a stomach tube, followed by monitoring and counting dead mice for an additional 7 days to determine respective $LD_{50}$ value in accordance with the Van der Waerden's method.

The results were as shown in Table VII.

TABLE VII

| | $LD_{50}$ | |
|---|---|---|
| Compound No. | Intraperitoneal administration (mg/kg body weight) | Oral administration (g/kg body weight) |
| 1 | 34 | 4.0 or higher |
| 2 | 30 | 4.0 or higher |
| 3 | 31 | 4.0 or higher |
| 4 | 37 | 4.0 or higher |
| 5 | 28 | 4.0 or higher |
| 6 | 65 | 4.0 or higher |
| 7 | 84 | 4.0 or higher |
| 8 | 40 | 4.0 or higher |

The results in Table VII evidently confirm that the $LD_{50}$ values on intraperitoneal administration fall in the range of 28–84 mg/kg (body weight), while those on oral administration are 4.0 g/kg (body weight) or higher. These $LD_{50}$ values and the fact that the cyanine dye used in this invention is efficacious in a dose of 0.5–50 μg/kg (body weight) suggest that the antitumor agent of this invention has a very wide safety margin.

Several embodiments wherein respective cyanine dye in Table I is incorporated as the effective ingredient will be described hereinafter.

EXAMPLE 1

Tablet

Tablets were prepared in usual manner, each tablet containing 0.1 mg of either of Compounds No. 1–8 in Table I, 79.9 mg lactose, 62.5 mg cornstarch and 7.5 mg fatty acid ester of sucrose.

In case of gastric coated tablets, the above tablets were further subjected to 5% by weight coating of hydroxypropyl methylcellulose, followed by sugar coating. While in case of enteric coated tablets, the above tablets were subjected first to 10% by weight coating of hydroxypropyl methylcellulose phthalate, then to sugar coating.

The products are favorably usable in the treatment of stomach cancer, lung cancer, liver cancer, uterine cancer, breast cancer, large bowel cancer, colon cancer and malignant melanoma.

EXAMPLE 2

Capsule

Capsules were prepared in usual manner, each capsule containing 0.2 mg of either of Compounds No. 1–8 in Table I, 146.8 mg lactose and 3.0 mg fatty acid ester of sucrose.

The product is favorably usable in the treatment of stomach cancer, lung cancer, liver cancer, uterine cancer, breast cancer, large bowel cancer, colon cancer and malignant melanoma.

EXAMPLE 3

Injection

An injection was prepared in usual manner by mixing 5 mg of either of Compound No.1–8 in Table I with 5 g sodium bicarbonate, and distributing 0.1 g aliquots of the mixture in sterilized glass vials.

The product is favorably usable as a ready-mix-type injection in the treatment of stomach cancer, lung cancer, liver cancer, uterine cancer, breast cancer, large bowel cancer, colon cancer and malignant melanoma.

EXAMPLE 4

Endermic Composition

An endermic composition was prepared in usual manner by first mixing either of Compounds No.1–8 in Table I with a small amount of liquid paraffin to homogeneity, then further mixing the resultant with vaseline to give an effective ingredient content of 5 mg/g.

The product is favorably usable as an ointment in the treatment of skin cancer, breast cancer and lymphoma.

EXAMPLE 5

Powdery Composition

A powdery composition was prepared in usual manner, one dose containing 0.3 mg of either of Compounds No.1–8 in Table I and 499.7 mg sodium bicarbonate.

11

The product is advantageously usable in the treatment of stomach cancer, lung cancer, liver cancer, uterine cancer, breast cancer, large bowel cancer, colon cancer and malignant melanoma.

EXAMPLE 6

Suppository

A suppository was prepared in usual manner, one dose containing 0.3 mg of either of Compounds No.1–8 in Table I, 1280 mg polyethylene glycol #1000 and 319.70 mg polyethylene glycol #4000.

The product is advantageously usable in the treatment of large bowel cancer and colon cancer.

As described above, the present invention relates to a novel BRM antitumor agent wherein the specified cyanine dye is incorporated as the effective ingredient, based on the finding that the cyanine dye remarkably activates macrophages in vivo which specifically attack tumoral tissues.

Accordingly, the antitumor agent of this invention is characterized in that it attains the objective in a small dose, as well as that it causes less side effect even when administered for long time because, unlike conventional antitumor agents utilizing any cytotoxicity of compounds, the present antitumor agent does not affect normal cells.

Furthermore, patients do not necessarily apply an injection by themselves because, unlike proteinaceous BRMs from animal cells, the antitumor agent of this invention attains an extremely high antitumor effect even through oral administration.

In addition, the antitumor agent of this invention attains a much higher antitumor effect when a tumoral tissue is marked so that macrophages readily recognizes the tumoral tissue either by making a slight damage or burn in the tumoral site; by irradiating an electromagnetic wave or radiation such as infrared rays; by administering a reduced concentration of other antitumor agent or BCG vaccine; or by using in combination hyperthermia.

This invention attains such a remarkable effect, and would make a great contribution to the art.

12

We claim:

1. A method for activating macrophages in a mammal comprising:

administering to said mammal, an amount sufficient for said activation of a cyanine dye of the formula:

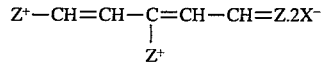

wherein $X^-$ is a physiologically-acceptable anion selected from the group consisting of chloride, bromide, iodide, sulfuric ion, nitric ion, perchloric ion, p-toluenesulfonic ion, acetic ion, nicotinic ion and orotic ion; $Z^+$ is a group of the formula:

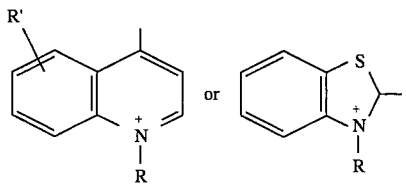

R is an alkyl group having a carbon chain length of 1–5; and R' is either hydrogen atom or an alkoxy group, said administration being carried out at a dose of about 0.1–50 μg/kg/day for said mammal.

2. A method according to claim 1 wherein R is ethyl.

3. A method in accordance with claim 1 wherein said administration is by injection.

4. The method according to claim 1 wherein said administration is oral.

5. A method according to claim 1, wherein said mammal is a human.

6. The method of claim 1, wherein said cyanine dye is [bis-4-(1-ethylquinoline)] [γ-4'-(1-ethylquinotine)] pentamethine cyanine diiodie.

* * * * *